(12) United States Patent
Fauconet et al.

(10) Patent No.: US 10,961,179 B2
(45) Date of Patent: Mar. 30, 2021

(54) PROCESS FOR PRODUCING POLYMER-GRADE (METH)ACRYLIC ACID

(71) Applicant: Arkema France, Colombes (FR)

(72) Inventors: Michel Fauconet, Valmont (FR); Sandeep Jain, Paris (FR)

(73) Assignee: Arkema France, Colombes (FR)

(*) Notice: Subject to any disclaimer, the term of this patent is extended or adjusted under 35 U.S.C. 154(b) by 0 days.

(21) Appl. No.: 15/765,496

(22) PCT Filed: Sep. 26, 2016

(86) PCT No.: PCT/FR2016/052434
§ 371 (c)(1),
(2) Date: Apr. 3, 2018

(87) PCT Pub. No.: WO2017/060583
PCT Pub. Date: Apr. 13, 2017

(65) Prior Publication Data
US 2019/0071382 A1 Mar. 7, 2019

(30) Foreign Application Priority Data

Oct. 6, 2015 (FR) ..................................... 1559493

(51) Int. Cl.
| C07C 57/04 | (2006.01) |
| C07C 51/44 | (2006.01) |
| C08F 20/06 | (2006.01) |
| C07C 51/487 | (2006.01) |
| C07C 51/46 | (2006.01) |

(52) U.S. Cl.
CPC .............. *C07C 51/44* (2013.01); *C07C 51/46* (2013.01); *C07C 51/487* (2013.01); *C08F 20/06* (2013.01); *C07C 57/04* (2013.01)

(58) Field of Classification Search
CPC ....... C07C 51/44; C07C 51/487; C07C 57/04; C07C 51/46; C08F 20/06
See application file for complete search history.

(56) References Cited

U.S. PATENT DOCUMENTS

| 3,725,208 | A | 4/1973 | Maezawa et al. |
| 4,828,652 | A | 5/1989 | Schropp |
| 5,504,247 | A | 4/1996 | Saxer et al. |
| 5,746,892 | A | 5/1998 | Bauer, Jr. et al. |
| 5,759,358 | A | 6/1998 | Bauer, Jr. et al. |
| 5,831,124 | A | 11/1998 | Machhammer et al. |
| 6,179,966 | B1 * | 1/2001 | Shimizu .................. C07C 51/46 159/47.1 |
| 6,414,192 | B1 | 7/2002 | Schelhaas et al. |
| 6,448,439 | B1 | 9/2002 | Eck et al. |
| 6,482,981 | B2 | 11/2002 | Ueno et al. |
| 7,048,834 | B2 | 5/2006 | Ishii et al. |
| 2004/0015014 | A1 | 1/2004 | Nishimura et al. |
| 2006/0205979 | A1 * | 9/2006 | Yada ....................... C07C 51/44 562/600 |
| 2009/0253934 | A1 * | 10/2009 | Ho .......................... C07C 51/44 562/600 |
| 2012/0006673 | A1 * | 1/2012 | Lee .......................... B01D 3/14 203/87 |
| 2012/0226074 | A1 | 9/2012 | Ho et al. |
| 2013/0165690 | A1 * | 6/2013 | Fauconet ................ C07C 45/52 562/532 |
| 2014/0066652 | A1 * | 3/2014 | Miyamoto .............. C07C 51/43 562/600 |

FOREIGN PATENT DOCUMENTS

| EP | 2 066 613 B1 | | 6/2012 |
| JP | 2002179617 | * | 6/2002 |
| JP | 2002179617 A2 | | 6/2002 |

OTHER PUBLICATIONS

JP2002179617 translation 2002 (Year: 2002).*

* cited by examiner

*Primary Examiner* — Yevgeny Valenrod
*Assistant Examiner* — Blaine G Doletski
(74) *Attorney, Agent, or Firm* — Lynn B. Morreale (57) ABSTRACT

A process for the recovery of polymer-grade (meth)acrylic acid, in the absence of organic solvent, from a gaseous reaction mixture comprising (meth)acrylic acid obtained by gas-phase oxidation of a precursor of the (meth)acrylic acid, the process carried out in a plant comprising at least one dehydration column and one finishing column, being characterized by the presence of at least one chemical treatment agent targeted at reducing the content of residual aldehydes. (Meth)acrylic acid obtained according to the invention meets criteria of high quality allowing it to be used in the manufacture of acrylic polymers, in particular for superabsorbents. This grade is also known as glacial acrylic acid GAA.

8 Claims, 2 Drawing Sheets

PROCESS FOR PRODUCING POLYMER-GRADE (METH)ACRYLIC ACID

CROSS-REFERENCE TO RELATED APPLICATIONS

This application is a national stage application under 35 U.S.C. § 371 of PCT/FR2016/052434, filed Sep. 26, 2016 which claims benefit to application FR15.59493, filed Oct. 6, 2015.

TECHNICAL FIELD

The present invention relates to the production of polymer-grade (meth)acrylic acid. The term "polymer-grade" indicates that the acrylic acid meets criteria of high quality allowing it to be used in the manufacture of acrylic polymers, in particular for the field of superabsorbents. This grade is also known under the term of glacial acrylic acid GAA.

A subject-matter of the invention is more particularly a process for the recovery/purification of polymer-grade (meth)acrylic acid from a crude reaction mixture comprising (meth)acrylic acid, the said process not using an organic solvent or a crystallization treatment, and including a treatment using a chemical agent targeted at reducing the content of residual aldehydes.

The invention also relates to a plant suitable for the implementation of the said recovery/purification process, and also to a process for the production of polymer-grade (meth)acrylic acid.

TECHNICAL BACKGROUND AND TECHNICAL PROBLEM

Acrylic acid is intended essentially for use by industrialists of polymerization processes (or copolymerization processes in the presence of other polymerizable monomers), either of acrylic acid as is or of its derivatives in the form of salts (for example sodium acrylate), esters (alkyl acrylates) or amides (acrylamide). These processes are carried out under different forms, in bulk, in solution, in suspension or in emulsion.

The polymerization and/or copolymerization processes involving acrylic acid can be very sensitive to the presence in the feedstock of certain impurities, such as unsaturated compounds or aldehydes, which can sometimes prevent the expected usage value from being obtained, for example by limiting the conversion of the monomer into polymer, by limiting the chain length of the polymer, by causing cross-linking reactions or since they modify the reactivity of the reaction.

Some of these impurities, such as nonpolymerizable saturated compounds, can also be particularly troublesome in the final application of the polymer, since they modify the properties of the polymer, confer toxic or corrosive properties on the polymer or also increase polluting organic discharges during the stages of manufacture of the polymer and/or of the finished product.

Consequently, users of acrylic acid or of acrylic acid derivatives are demanding as regards quality specifications of acrylic acid. The latter has to meet strict thresholds as regards impurities.

In addition, these users employ formulations for the production of their polymers which are suited to a "standard" quality of acrylic acid or its derivatives. A modification to the formulations used by these users, for the purpose of adapting them to a different quality of acrylic acid, would exhibit major disadvantages for these user companies.

As the quality (or the purity) of the acrylic acid, that is to say its content of various impurities, plays a major role in polymerization processes, the industrialists who manufacture this acrylic acid have been led to deploy a whole series of purification stages in order to obtain this "standard" acrylic acid, which is normally referred to as polymer-grade acrylic acid or glacial acrylic acid (GAA). This GAA does not meet specifications which are recognized officially and which have a universal nature but signifies, for each industrialist, the level of purity to be achieved in order to be able to successfully carry out its polymerization in the acid form or in the form of a derivative and to obtain polymers compatible with their final uses.

The processes for the recovery/purification of acrylic acid described in the prior art are very complex when it is a matter of producing polymer-grade acrylic acid and exhibit numerous disadvantages.

This is because the processes for the synthesis of acrylic acid always result in a gaseous reaction medium consisting of a complex mixture of impurities, generally classified according to their property of being condensed to give a liquid mixture or of being absorbed in a liquid mixture, or classified according to their boiling point with respect to that of acrylic acid (light compounds or heavy compounds).

It follows that the purification processes normally use a combination of operations in order to separate and recover the acrylic acid present in this gaseous effluent.

Some of these operations employ one or more organic solvents as absorption agents (gas/liquid exchanges) and/or as agents for extraction into a liquid medium (liquid/liquid exchanges) and/or also as agents for separation by azeotropic distillation. These processes, which include in particular, in addition to the stages of separation of the desired product, treatment stages for recovery and purification of the solvents, necessarily involve a large number of distillation columns, resulting in a technical acrylic acid in which the content of impurities has been greatly reduced but which does not satisfy the specifications of a glacial acrylic acid necessary in order to obtain, for example, polymers of high molecular weight.

Other processes, such as, for example, that described in patent EP 2 066 613 B1, make it possible to simplify the recovery and the purification of acrylic acid by very significantly reducing the number of individual operations necessary for the purified product to be obtained. These processes are characterized in that they do not involve any addition of organic solvent external to the process and in that they use a restricted number of distillation columns, in particular less than three columns. These simplified processes make it possible to obtain a quality of technical acrylic acid of high purity, which can reach or exceed 99%, but still not sufficient for the most demanding applications of acrylic acid requiring polymers of high molecular weights, for which a quality of glacial (or polymer-grade) acrylic acid is required.

In order to achieve a quality of glacial acrylic acid, it is necessary to remove, up to a very exhaustive level (at most a few ppm), certain impurities still present in the technical acrylic acid obtained according to the abovementioned processes.

There are in particular certain aldehydes, such as furfuraldehyde, benzaldehyde and acrolein, or other impurities, such as protoanemonin, a heavy compound generated during the synthesis of acrylic acid, or also nonphenolic polymerization inhibitors, such as phenothiazine, liable to have been introduced during the synthesis of the (meth)acrylic acid.

These impurities can be removed by an additional treatment stage using fractional crystallization, as described, for example, in the documents U.S. Pat. No. 6,448,439 or EP 2 066 613 B1.

Fractional crystallization is a well known separation technique. It can be carried out in different forms: dynamic crystallization, static crystallization or suspension crystallization (U.S. Pat. Nos. 5,504,247; 5,831,124; 6,482,981).

However, the additional purification by fractional crystallization is expensive in capital costs and in energy required for the successive phases of cooling and heating.

For this reason, additional processes for purification by distillation are commonly used for the removal of the impurities from technical acrylic acid. However, this removal, down to extremely low contents of a few ppm, cannot be economically obtained by simple distillation, due, on the one hand, to their high concentrations with respect to the threshold of their sensitivity with regard to the polymerization reactivity and, on the other hand, to the volatility of some of these compounds, which is too close to that of acrylic acid.

In order to do this, industrialists generally use processes combining a purification by distillation and a chemical treatment using a reactant which forms, with the aldehydes, heavy reaction products which can be more easily separated from the acrylic acid by distillation.

Among the reactants which can be used, it is possible to employ, for example, amines, compounds of the family of the hydrazines or aminoguanidine, which are used as is or in the form of their salts, or as a mixture (U.S. Pat. No. 3,725,208; EP 270999; EP 685448).

The chemical treatments which are described in the prior art all exhibit the disadvantage of generating water during the reaction of the aldehydes with the reactant. The presence of water in the acrylic acid can also be damaging for the manufacture of certain polymers.

For this reason, provision has been made, in the document JP 49-95,920, to carry out this chemical treatment during a distillation stage targeted at removing the water and the light compounds at the top, before a stage of distillation of the acrylic acid intended to separate the heavy compounds.

In the purification process described in the document JP 2002 179627, the chemical treatment of the aldehydes is carried out in a static mixer.

These various techniques combining a purification of the acrylic acid of technical grade by distillation and chemical treatment of the aldehydes are described in particular for the purification of the technical acrylic acid obtained by conventional processes involving at least one external organic solvent. They have the disadvantage of requiring an additional purification section, with at least one additional distillation column equipped with its ancillary parts (reboiler, condenser, pumps, and the like), which has a negative impact on the cost of the industrial unit and also on the energy consumption.

In addition, the chemical treatment of the aldehydes is generally accompanied by the formation of solids which gradually accumulate and require frequent cleaning operations on the items of equipment, negatively impacting the productivity of the plant.

According to the process for the purification of acrylic acid described in patent EP 1110940 of Nippon Shokubai, it is necessary to adjust the ratio of concentration of furfural to acrolein by weight present in the acrylic acid to be treated to between 3 and 100, so as to improve the effectiveness of the treatment for the removal of aldehydes by a chemical agent of hydrazine type. Under these conditions, the amount of chemical agent to be introduced is reduced and the formation of polymers is limited.

A need thus remains to have available a process for the recovery/purification of acrylic acid resulting in a quality of acrylic acid of polymer (or glacial) grade which is simplified, fast and easy to carry out (comprising as few stages as possible), which does not require the involvement of organic and/or azeotropic solvent, or of technology which is expensive in energy or polluting, and which in addition does not result in the formation of polymers which foul the items of equipment.

The inventors have now discovered that this need could be met by employing a section for purification of an acrylic acid gaseous reaction mixture without addition of external organic solvent and without treatment by crystallization, in particular in a plant comprising a dehydration column and a finishing column (or purification column) fed with a portion of the bottom stream from the dehydration column, and including a stage of treatment of the aldehydes using a chemical agent preferably carried out inside the abovementioned purification section, or alternatively in an additional purification section using distillation, making it possible to result directly in a glacial acrylic acid quality.

Furthermore, it is apparent to the inventors that this invention could be applied to the acrylic acid and to the methacrylic acid which are produced from different sources, and also to these acids derived from renewable starting materials, which are liable to present the same problems of purification.

SUMMARY OF THE INVENTION

The present invention relates to a process for the recovery of polymer-grade (meth)acrylic acid, in the absence of organic solvent, from a gaseous reaction mixture comprising (meth)acrylic acid obtained by gas-phase oxidation of a precursor of the (meth)acrylic acid, comprising at least the following stages:
i) the gaseous reaction mixture is subjected to dehydration without using azeotropic solvent in a first distillation column, referred to as dehydration column, resulting in a top stream, at least a portion of which is condensed and sent back to the dehydration column in the form of reflux, and in a bottom stream;
ii) the dehydration column bottom stream is subjected, at least in part, to distillation in a second column, referred to as finishing column, resulting in a top stream and in a bottom stream comprising heavy compounds;
iii) a purified (meth)acrylic acid stream is recovered by drawing off a sidestream from the finishing column; characterized in that it is carried out in the presence of at least one agent for the chemical treatment of the aldehydes.

According to certain specific embodiments, the agent for the chemical treatment of the aldehydes is introduced into the finishing column or at the bottom of the dehydration column, and the purified (meth)acrylic acid stream drawn off in stage iii) is a gaseous stream of polymer-grade (meth) acrylic acid.

According to other specific embodiments, the purified (meth)acrylic acid stream drawn off in stage iii) is subjected to an additional treatment by distillation using one or two distillation column(s) and the introduction of the agent for the chemical treatment of the aldehydes is carried out during the said treatment, thus resulting in a polymer-grade (meth) acrylic acid stream.

In the present invention, the term "(meth)acrylic" means "acrylic" or "methacrylic".

The term "azeotropic solvent" denotes any organic solvent exhibiting the property of forming an azeotropic mixture with water.

The term "noncondensable" denotes the compounds for which the boiling point is lower than the temperature of 20° C. at atmospheric pressure.

The term "light", describing the byproduct compounds, denotes the compounds for which the boiling point is lower than that of (meth)acrylic acid under the working pressure considered and, analogously, the term "heavy" denotes the compounds for which the boiling point is greater than that of (meth)acrylic acid.

The term "agent for the chemical treatment of the aldehydes" means a chemical agent which makes it possible to reduce, down to a very low level, the content of the aldehydes present in the medium to be treated.

The term "polymer-grade" indicates that the acrylic acid meets criteria of high quality allowing it to be used in the manufacture of acrylic polymers of high molecular weight.

The process according to the invention can additionally comprise other preliminary, intermediate or subsequent stages, provided that they do not negatively affect the production of polymer-grade (meth)acrylic acid.

According to certain specific embodiments, the invention also exhibits one or preferably several of the advantageous characteristics listed below:

the agent for the chemical treatment of the aldehydes is introduced into the finishing column via the feed stream of the said column;

the agent for the chemical treatment of the aldehydes is introduced directly into the finishing column at the level of a section located between the feed level of the said column and the level of the plate for drawing off a sidestream of purified (meth)acrylic acid;

the agent for the chemical treatment of the aldehydes is introduced at the bottom of the dehydration column, preferably in the liquid stream brought into contact with the gaseous reaction stream for the purpose of the cooling thereof;

the agent for the chemical treatment of the aldehydes is introduced during an additional treatment by distillation of the stream drawn off as a sidestream from the finishing column;

the agent for the chemical treatment of the aldehydes is introduced into the plant via a mixing device comprising at least one tank ensuring the intimate mixing of the chemical agent with the stream to be treated and providing the most appropriate conditions for an effective treatment. In this mode of operation, the tank ensures the mixing of the reactants with the (meth)acrylic acid stream containing the aldehyde impurities to be removed and the chemical treatment can be carried out under conditions of temperature and of residence time which make possible optimum effectiveness;

the finishing column is a conventional distillation column;

the finishing column is a column having a separating wall fed, on one side of the wall, with the dehydration column bottom stream and the drawing off a sidestream of the purified (meth)acrylic acid stream is carried out in the gas or liquid phase in the section located on the other side of the separating wall. The finishing column top stream is sent back, in part, at the top of this column, in order to ensure liquid reflux in the section delimited by the separating wall comprising the drawing off of a sidestream;

a second drawing off in the gas phase on the finishing column is carried out at a position located below the drawing off of a sidestream of purified acrylic acid.

According to one embodiment of the invention, the precursor of the (meth)acrylic acid is acrolein.

According to one embodiment of the invention, the acrolein is obtained by oxidation of propylene or by oxydehydrogenation of propane.

According to one embodiment of the invention, the precursor of the (meth)acrylic acid is methacrolein.

According to one embodiment of the invention, the methacrolein is obtained by oxidation of isobutylene and/or of tert-butanol.

According to one embodiment of the invention, the methacrolein is obtained from oxydehydrogenation of butane and/or isobutane.

According to one embodiment of the invention, the gaseous reaction mixture comprising (meth)acrylic acid obtained by gas-phase oxidation of a precursor of the (meth)acrylic acid comprises carbon of renewable origin.

According to one embodiment of the invention, the precursor of the (meth)acrylic acid is derived from glycerol, 3-hydroxypropionic acid or 2-hydroxypropionic acid (lactic acid).

According to a preferred embodiment of the invention, the gaseous reaction mixture comprises acrylic acid derived from propylene obtained according to a two-stage oxidation process.

The recovery process according to the invention produces a stream of polymer-grade (meth)acrylic acid, corresponding to a quality satisfactory for producing polymers of high molecular weight, which can be used, for example, as superabsorbents. The process according to the invention does not require the use of an external organic solvent in order to remove the water present in the gaseous reaction mixture comprising the (meth)acrylic acid. The process according to the invention does not employ a crystallization treatment. In a preferred mode of operation, the process according to the invention requires, starting from the gaseous reaction mixture, only a purification section based on two distillation columns including a stage of treatment of the aldehydes using a chemical agent, carried out inside the said section.

Another subject-matter of the present invention is a plant for recovering polymer-grade (meth)acrylic acid suitable for implementing the process according to the invention.

The plant according to the invention comprises at least:
a) one dehydration column;
b) one finishing column fluidically connected at the bottom of the said dehydration column;
c) optionally at least one distillation column fluidically connected laterally to the said finishing column;
d) a mixing device ensuring the introduction, the mixing and the optimum conditions for reaction of the chemical treatment agent in the dehydration column bottom stream feeding the finishing column, optionally comprising an intermediate tank;
e) at least one system for drawing off a sidestream for the finishing column.

It is desired, by "fluid connection" or "fluidically connected", to indicate that there is connection by a system of pipes capable of transporting a stream of material. This connection system can comprise valves, bypasses, heat exchangers or compressors.

"Intermediate tank" denotes a chamber which can contain a certain volume of liquid, fed with a liquid stream passing in intermediate transit through this tank before being sent to the following stage of the process.

"Mixing device" is understood to mean a combination of items of equipment in series which ensures the most efficient dispersion of the chemical treatment agent in the stream to be treated and the conditions of residence time and temperature which make it possible to obtain optimum effectiveness of the reaction.

Another subject-matter of the invention is a process for the production of polymer-grade (meth)acrylic acid comprising at least the following stages:
A) at least one (meth)acrylic acid precursor is subjected to gas-phase oxidation in order to form a gaseous reaction mixture comprising (meth)acrylic acid;
B) the gaseous reaction mixture is cooled;
C) the cooled gaseous reaction mixture is subjected to the process for the recovery of polymer-grade (meth) acrylic acid as defined above.

The present invention makes it possible to produce polymer-grade (meth)acrylic acid in an overall process not employing an organic solvent, thus reducing the energy costs of recovery and the discharges, with respect to a conventional process with an organic solvent. The process according to the invention employs a simpler technology than batchwise fractional crystallization or than continuous crystallization in suspension.

In its preferred mode of operation, that is to say without an additional distillation column with respect to the process of the prior art producing a quality of (meth)acrylic acid of technical grade, the present invention makes it possible in addition to further reduce the capital costs and the energy costs of purification for producing polymer-grade or glacial (meth)acrylic acid. Furthermore, as the formation of solid polymers which foul the items of equipment is avoided, the invention introduces the possibility of producing per campaign, on the same plant, different qualities of (meth)acrylic acid, according to the use or not of the chemical treatment of the aldehydes, which provides industrialists with a degree of operational flexibility.

DESCRIPTION OF THE DRAWINGS

Other characteristics and advantages of the invention will more clearly emerge on reading the detailed description which follows, with reference to the appended FIGS. 1 to 4, which represent.

DETAILED DESCRIPTION OF THE INVENTION

For the sake of simplicity, the continuation of the account will refer to the production of acrylic acid but also applies analogously to the production of methacrylic acid.

The invention is targeted at producing high-purity acrylic acid and is based on the use of a treatment using a chemical agent targeted at removing, down to a very exhaustive level (at most a few ppm), certain impurities still present in the technical acrylic acid obtained according to a process not using an external organic solvent. They are in particular aldehydes, the presence of which, even in the form of traces, is harmful to the attainment of acrylic polymers of high molecular weight.

In the continuation of the account of the invention, the term "chemical treatment" is understood to mean the treatment carried out using the agent for the chemical treatment of the aldehydes.

According to a first aspect of the invention, the chemical treatment is incorporated in a process for the recovery of technical acrylic acid, thus resulting directly in a quality of acrylic acid of polymer grade. The preferred embodiments are represented in FIGS. 1 and 2.

Figure 3:
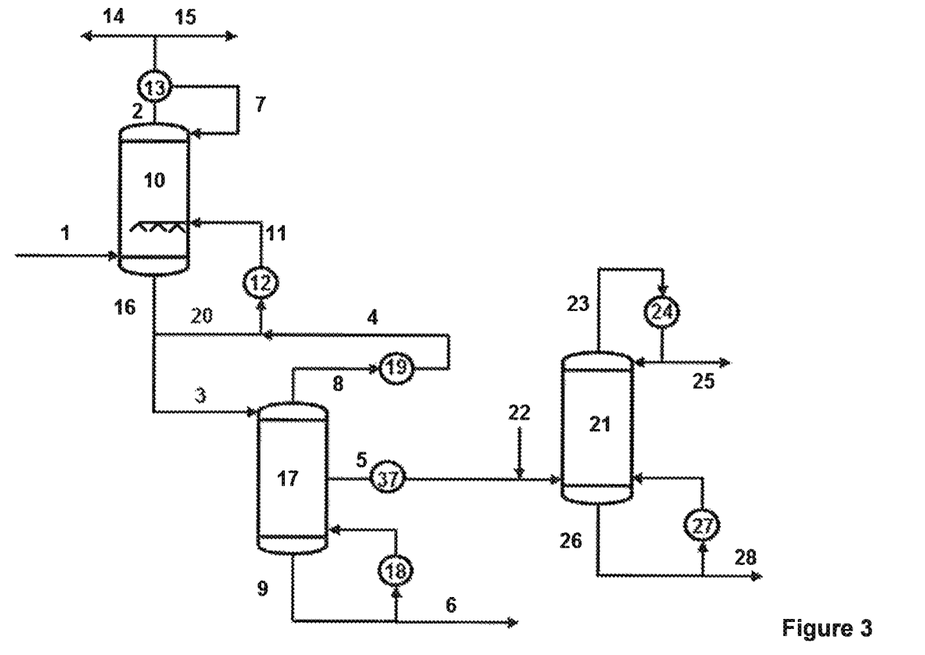
FIG. 3: Plant suitable for the implementation of the process for the recovery of polymer-grade acrylic acid using an additional purification section employing distillation using a distillation column.
Figure 4:
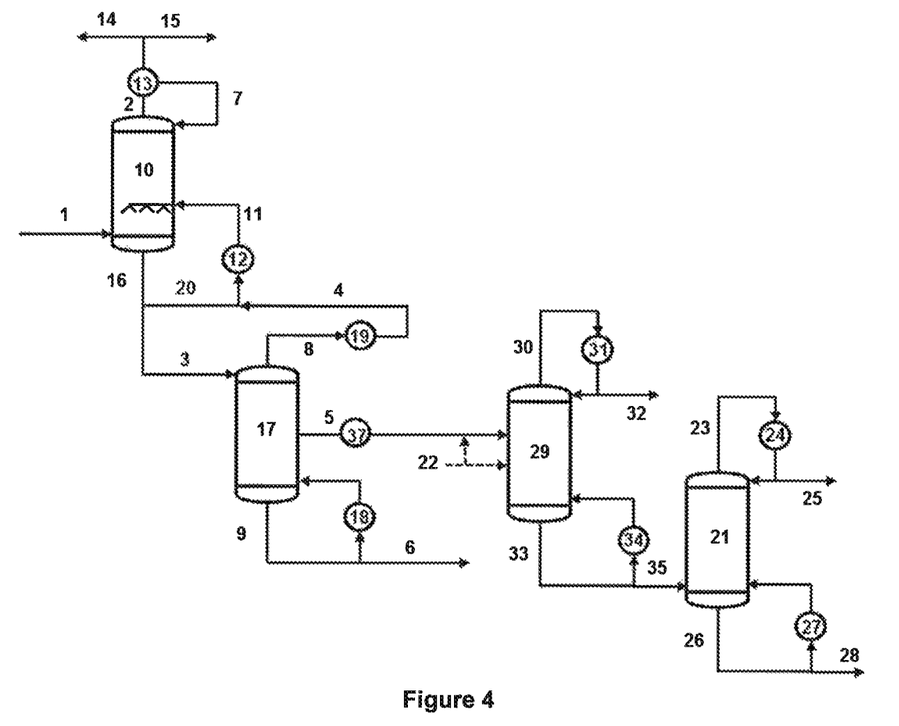
FIG. 4: Plant suitable for the implementation of the process for the recovery of polymer-grade acrylic acid using an additional purification section employing distillation using two distillation columns.

Alternatively, according to a second aspect of the invention, the technical acrylic acid is subjected to a chemical treatment during an additional treatment by distillation using one or two distillation columns, as represented in FIGS. 3 and 4.

Figure 1:
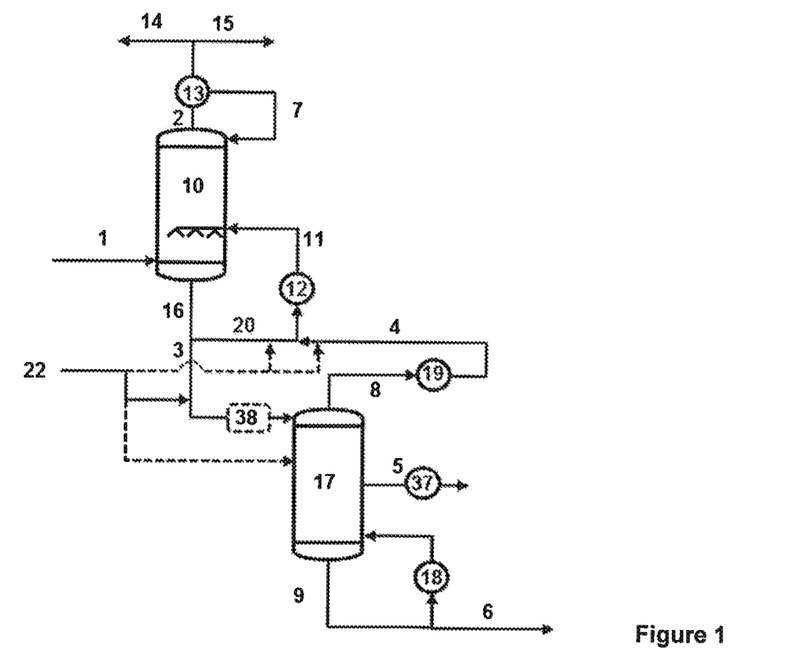
FIG. 1: Plant appropriate for the implementation of the process for the recovery of polymer-grade acrylic acid illustrating a preferred embodiment of the invention, using a conventional distillation column as finishing column.
Figure 2:
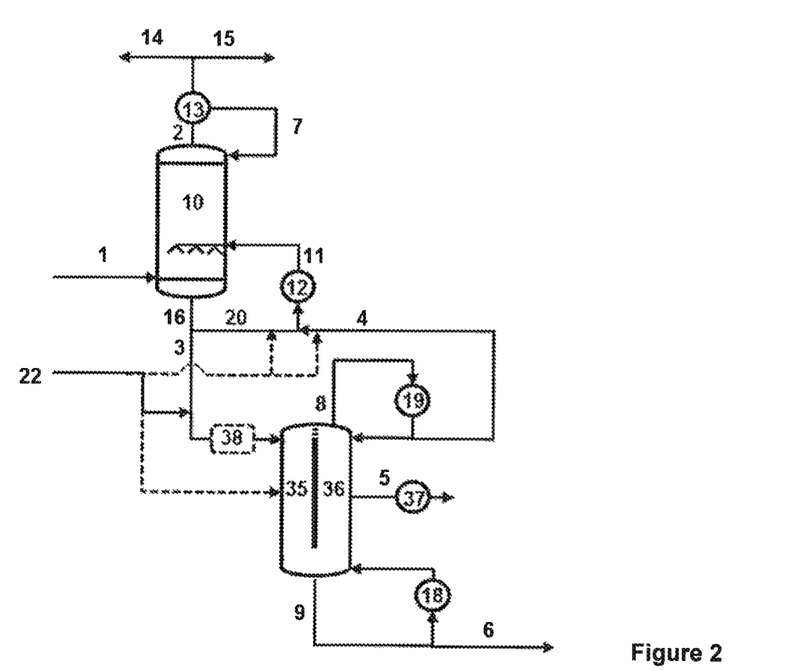
FIG. 2: Plant appropriate for the implementation of the process for the recovery of polymer-grade acrylic acid illustrating a second preferred embodiment of the invention, using a distillation column having a separating wall as finishing column.

According to a first embodiment of the invention represented in FIG. 1, a gaseous reaction mixture 1 comprising acrylic acid obtained by gas-phase oxidation of an acrylic acid precursor feeds a first distillation column 10. The gaseous reaction mixture, which comprises a water/acrylic acid ratio by weight generally of between 0.3 and 2, can be precooled before being subjected to as dehydration according to stage i) of the process according to the invention in the column 10 referred to as dehydration column.

The reaction mixture comprises, in addition to the water and the acrylic acid, noncondensable light products, such as nitrogen, oxygen, carbon monoxide and carbon dioxide, and also various light or heavy byproducts of different chemical nature which can be light aldehydes, such as acrolein, formaldehyde or acetaldehyde, heavy aldehydes such as furfuraldehyde or benzaldehyde, light acids, such as formic acid, acetic acid or propionic acid, or heavy acids, such as maleic acid, benzoic acid or 2-butenoic acid.

The dehydration column results in a top stream 2, at least a portion of which is condensed in a condenser 13 and sent back to the dehydration column in the form of reflux 7 in order to absorb the acrylic acid, the other portion 14/15 comprising the noncondensable light compounds generally being sent partially or completely to a purification device or partly recycled to other stages of the process for the production of acrylic acid, preferably in a stage located upstream of the reactor for the production of the reaction mixture 1.

According to one embodiment, all of the top stream 2 from the dehydration column is sent to the top condenser 13.

The aim of the dehydration stage i) is to remove, in a top stream, the bulk of the water present in the reaction mixture but also the noncondensable light compounds and the condensable light compounds. The dehydration column operates, at least partially, as a distillation column. It is fed in its lower part with the reaction mixture 1. It generates a top stream 2 comprising the bulk of the water and of the light compounds, and acrylic acid and heavy compounds in a very small amount, and a bottom stream 16 depleted in light compounds comprising the bulk of the acrylic acid with heavy byproducts.

The dehydration column generally comprises from 5 to 50 theoretical plates, preferably from 20 to 30 theoretical plates. It is equipped with a heat exchanger, the main role of which, in the configuration represented in FIG. 1, is, according to the temperature of the gas 1 entering the column, to cool or heat the liquid stream 20 extracted from the column bottom, before sending it back as reflux into the lower part of the dehydration column. In another possible configuration not represented in FIG. 1, the gaseous stream 1 is precooled in an external exchanger before re-entering the dehydration column, and/or the gaseous stream 1 is cooled and condensed with reflux for a portion of the liquid stream 16, in a heat exchanger located outside the dehydration column, before being introduced into this column.

Advantageously, the dehydration column operates at atmospheric or slightly greater pressure, up to an absolute pressure of $1.5 \times 10^5$ Pa.

Advantageously, the temperature in the upper part of the dehydration column is at least 40° C., preferably between 40° C. and 80° C. The temperature of the bottom stream from the dehydration column preferably does not exceed 120° C.

According to the invention, the bulk of the water present in the gaseous reaction mixture comprising the acrylic acid is removed during stage i) without there being excessive loss of acrylic acid in the top stream 14/15.

No azeotropic solvent is added to the dehydration column.

The content by weight of water in the bottom stream from the dehydration column is generally less than 10%, preferably less than 7%. A typical composition by weight of the bottom stream from the dehydration column essentially comprises acrylic acid (84-90%), acetic acid (5-10%) and water (3-6%).

According to stage ii) of the process according to the invention, the bottom stream 16 from the dehydration column is sent, at least in part, (stream 3), to the top of a second distillation column 17, referred to as purification column or finishing column, in which a top stream 8 and a bottom stream 9 are separated.

According to one embodiment, a portion 20 of the bottom liquid stream 16 from the dehydration column is sent into a heat exchanger 12 which can be a heater or a cooler and reinjected into the dehydration column, so as to constitute a bottom loop. Preferably, the portion 11 of the bottom loop is reinjected between the feed of the gaseous reaction mixture and the dehydration column top. The remainder (stream 3) of the liquid stream 16 is sent as feed of the finishing column 17.

According to an optional alternative form of this embodiment, the stream 3 can be stored in an intermediate tank 38 before being sent as feed of the finishing column 17. In this option, it can be advantageous to cool the stream 3 with a heat exchanger located before the intermediate tank, or in an exchanger located on a loop recirculation circuit in this tank, and the cooled stream can subsequently be heated through an exchanger before being introduced into the purification column 17.

The gaseous top stream 8 from the purification column is sent into a condenser 19. The exiting liquid stream 4 is sent back to the dehydration column, between the bottom and the top of the column and preferably above the feed of the gaseous reaction mixture. According to one embodiment, as represented in FIG. 1, it is mixed with the stream from the bottom loop of the dehydration column.

The finishing column 17 makes it possible to separate a top stream 8 comprising water and the condensable light byproducts, a bottom stream 9 comprising the bulk of the heavy byproducts, in particular Michael addition products, such as 3-acryloyloxypropionic acid, maleic anhydride/acid, benzoic acid and also polymerization inhibitors, and a sidestream 5 comprising purified acrylic acid in the liquid or vapour form, preferably in the gaseous form.

The finishing column 17 can be a conventional distillation column generally comprising from 5 to 30 theoretical plates, preferably from 8 to 20 theoretical plates. This distillation column is combined with at least one reboiler and one condenser.

The temperature and the pressure in the column 17 are not critical and can be determined in accordance with the distillation methods known from the state of the art. However, preferably, the finishing column 17 operates at a pressure below atmospheric pressure, making it possible to operate at relatively low temperatures, thus preventing the polymerization of the unsaturated products present and minimizing the formation of heavy byproducts.

Advantageously, the finishing column operates under an absolute pressure ranging from 5 kPa to approximately 60 kPa, the temperature of the top stream advantageously being between 40° C. and approximately 90° C. and the temperature of the bottom stream being between 60° C. and 120° C.

In the absence of the chemical treatment according to the invention, the stream 5 of purified acrylic acid, drawn off as a sidestream from the finishing column, corresponds to a technical-grade acrylic acid.

According to a preferred configuration of the invention, a chemical agent 22 is introduced into the plant represented in FIG. 1, in order to directly produce a polymer-grade acrylic acid. It is possible for the introduction to be carried out in different ways.

According to a first embodiment described in FIG. 1, the chemical treatment agent 22 is introduced into the finishing column 17, either at the level of a section located between the feed level of the said column and the level of the plate for drawing off a sidestream, or preferably via the feed stream 3 of the said column.

According to other embodiments, the chemical treatment agent is introduced into the lower part of the dehydration column, at any point of the circuit for liquid stream 11 sent back into the column for the purpose of cooling and partially condensing the hot reaction gas. The addition can be carried out upstream or downstream of the heat exchanger 12. Another option also possible is to send the chemical treatment agent into the top stream 4 of column 17 recycled to the dehydration column.

The heavy products generated during the reaction of the chemical treatment agent with the aldehydes present in the stream feeding the dehydration column are removed first in the bottom stream 3 from the dehydration column and then finally in the bottom stream 9 from the finishing column, with the other heavy byproducts. The water produced by the reactions for the formation of these heavy products is removed partly at the top of the dehydration column and partly at the top of the finishing column.

The chemical treatment agent is a reactant which forms, with the aldehydes present in the stream feeding the finishing column, heavy reaction products which can be more easily separated from the acrylic acid. The reactions for the formation of these heavy products produce water, which is removed directly at the top of the finishing column, and the heavy products formed are removed in the bottom stream 9 from the finishing column with the other heavy byproducts.

Consequently, a gas stream 5 is drawn off as a sidestream from the finishing column, which, after condensation in an exchanger 37, forms a liquid stream of purified acrylic acid devoid of aldehydes, heavy compounds and non-phenolic polymerization inhibitors and also freed from water. It is thus a stream of acrylic acid freed from the impurities troublesome for its subsequent polymerization, corresponding directly to a quality of acrylic acid of polymer or glacial grade, which can be used to produce grades of polymers which are the most sensitive to impurities, such as, for example, superabsorbents, without the need for additional purification, in particular by fractional crystallization. A polymerization inhibitor can subsequently be added to this stream.

The bottom stream 9 from the finishing column 17 is partially sent back into this column through the reboiler 18. The other portion 6 can be sent to a concentration section (not represented in FIG. 1) for the purpose of recovering the residual acrylic acid monomer present in the stream 6, and/or sent into a cracking section for the purpose of regenerating the acrylic acid from the heavy Michael addition compounds of the 3-acryloyloxypropionic acid type, and/or be used as starting material in a unit for the production of acrylic esters.

In an alternative form, optionally, a second sidestream is drawn off in the gas phase on the finishing column 17 (not represented in FIG. 1), at a position located below the drawing off of a sidestream of purified polymer-grade acrylic acid. This stream concentrated in acrylic acid, freed from the bulk of the heavy products and reaction products of the chemical agent with the aldehydes, can advantageously be made use of economically as starting material of an esterification process for producing, for example, without limitation of choice, methyl acrylate, ethyl acrylate, butyl acrylate or 2-ethylhexyl acrylate.

In this alternative form, the second stream drawn off as a sidestream corresponds to an acrylic acid of intermediate quality, in particular of ester grade devoid of the heavy byproducts, which have been concentrated in the bottom stream 9 from the finishing column.

According to a preferred embodiment of the invention (represented in FIG. 1), the mixing of the agent for the chemical treatment of the aldehydes with the stream to be treated is carried out upstream of the finishing column in a mixing device 38 which makes possible the most effective dispersion of the agent for the chemical treatment of the aldehydes in the stream. This device can in particular contain, in series, one or more tanks and one or more items of mixing or heat exchange equipment, so as to carry out the treatment at an optimum temperature and for an optimum residence time.

Nonexhaustively, the items of mixing equipment can include devices generally used by a person skilled in the art to mix liquids, such as stirred or recirculated vessels or static mixers, but also all types of items of equipment which make possible rapid dispersion of the chemical treatment agent in the stream to be treated, such as axial jet mixers, rotary jet mixers, liquid jet ejectors, hydroejectors, pumps, filters, and the like.

According to this embodiment, preferably, the bottom stream from the dehydration column is cooled from 60-120° C. to 30-80° C. prior to or at the same time as the introduction of the agent for the chemical treatment of the aldehydes. One possible arrangement is that the bottom stream from the dehydration column is cooled and stored in intermediate fashion in a vat which is stirred or recirculated through a pump and the introduction of the agent for the chemical treatment of the aldehydes is carried out in this vat. The residence time in this intermediate tank is generally from 5 to 120 min. Prior to the feeding of the finishing column with the liquid mixture originating from this intermediate tank, the stream is preferably heated, if necessary, to a temperature of 70-90° C., in an in-line exchanger or heated intermediate tank.

These various embodiments, and in particular that combining a mixing arrangement, are particularly advantageous as they make it possible to reduce the amount of agent for the chemical treatment of the aldehydes necessary and reduce the fouling of the items of equipment by optimizing the reactivity of the treatment agent and by thus reducing the excess with respect to the aldehydes to be removed.

The agents for the chemical treatment of the aldehydes which can be used in the invention can be those described in the prior art for processes combining purification by distillation and chemical treatment of the aldehydes present in a technical acrylic acid.

They can be chemical agents employed alone or as a mixture in all proportions.

Mention may in particular be made of:
  amines, such as, for example, without limitation, monoethanolamine, ethylenediamine, glycine, diethylenetriamine, dipropylenetriamine, and ortho-, para-, and meta-phenylenediamine;
  compounds of the aniline family, such as, for example, without limitation, aniline, and ortho-, para-, and meta-methylaniline;
  compounds of the family of the hydrazines, such as, without limitation, hydrazine and its salts, hydrazine hydrate, hydrazine sulphate, hydrazine carboxylates, hydrazine hydrochloride, phenylhydrazine, 4-nitrophenylhydrazine, and 2,4-dinitrophenylhydrazine, or also aminoguanidine and its salts, such as aminoguanidine hydrogencarbonate;
  compounds of the family of the hydrazides, such as, for example, without limitation, hydrazides of carboxylic acids and their salts, such as hydrazides of formic acid, acetic acid, propionic acid, butanoic acid, pentanoic acid and maleic acid and dihydrazides of adipic acid and succinic acid, urea or derivatives of urea and of hydrazine, such as semicarbazide or carbohydrazide, and their salts;
  alone or their mixtures in all proportions.

The chemical agents are introduced as is into the stream to be treated or in solution in a solvent, for example in solution in acrylic acid.

The chemical agent is introduced in a minimum amount in order to obtain a quality of glacial acrylic acid sufficiently freed from the aldehyde impurities (in particular acrolein, furfuraldehyde and benzaldehyde) to meet the requirements of the clients. In general, the chemical agent is added in a molar ratio of 0.5 to 10, preferably of 1 to 5, with respect to the total aldehydes present in the medium to be treated.

With reference to FIG. 2 representing an alternative form of the invention, the finishing column 17 is replaced with a column having a separating wall comprising two sections 35 and 36, the section 35 being fed with the bottom stream 3 from the dehydration column and the stream 5 of polymer-grade acrylic acid being drawn off as a sidestream from the section 36.

In particular, the separating wall is not contiguous with the top part of the column; thus, the light compounds introduced by the stream 3 can be easily discharged in the stream 4 at the top of the column, after condensation of the gaseous stream 8 in the condenser 19.

These separating columns are sold in particular by Sulzer and Montz.

According to this embodiment, the chemical treatment agent 22 is introduced into the section 35 of the finishing column either via the feed stream 3 of the said column or at the level of a section located between the feed level of the said column in the section 35 and the bottom of this section, according to the various ways described above in connection with a conventional column.

The top stream 8 from this finishing column is condensed in the condenser 19 and sent back, in part, at the top of the finishing column in order to ensure a liquid reflux in the section 36 delimited by the separating wall comprising the drawing off of a sidestream, the other portion 4 being recycled in the bottom loop of the dehydration column. According to this configuration, the drawing off of a sidestream of the stream of polymer-grade (meth)acrylic acid is carried out in the gas phase and is then condensed in an exchanger 37, and polymerization inhibitor, such as hydroquinone methyl ether (HQME), is added at a content of 200+/−20 ppm. Advantageously, one or more polymerization inhibitors is (are) introduced into the liquid mixture sent back as reflux at the column top. In an alternative form, the drawing off of a sidestream of the stream of polymer-grade acrylic acid can be carried out in the liquid phase and the purified stream is cooled in the exchanger 37. In this case, HQME is introduced into the liquid mixture sent back as reflux at the column top, in an amount such that the concentration of this inhibitor in the stream of polymer-grade acrylic acid does not exceed 220 ppm.

According to a second aspect of the invention, no agent for the chemical treatment of the aldehydes is introduced into the purification section comprising the dehydration column 10 and the finishing column 17, and the stream 5 drawn off as a sidestream from the finishing column in the liquid or gaseous form and then cooled or condensed in the exchanger 37 is a stream of purified acrylic acid corresponding to a technical quality.

According to this aspect of the invention, some embodiments of which are represented in FIGS. 3 and 4, the purification of the technical acrylic acid to give polymer-grade acrylic acid is carried out in an additional purification section comprising either an additional purification column 21 equipped with a reboiler at the bottom and with a condenser at the top (FIG. 3) or two purification columns 29 and 21 equipped with a reboiler at the bottom and with a condenser at the top (FIG. 4).

In the configuration of FIG. 3, the chemical treatment agent 22 is introduced into the stream of technical acrylic acid 5 feeding the purification column 21. The column 21 is equipped with a boiler 27, through which a portion of the column bottom stream is sent back into the column, and with a top condenser 24. A portion of the purified top stream is sent back as reflux into the column 21. This column is preferably operated under reduced pressure.

The chemical treatment agent forms, with the aldehydes present in the stream 5, heavy reaction products which can be more easily separated from the acrylic acid and which are removed in the bottom stream 28 from the column 21. The water produced by the reactions for the formation of these heavy products is entrained with the acrylic acid in the top stream from the purification column 21. The top stream 25 thus corresponds to a quality of glacial (or polymer-grade) acrylic acid meeting the quality criteria required for the production of polymers intended for applications for which water is not a troublesome impurity. This is the case, for example, for the manufacture of superabsorbents, which employs a prior stage of dilution in water before partial neutralization and polymerization.

In the configuration of FIG. 4, the additional purification is carried out starting from two successive columns, so as to obtain a quality of acrylic acid of polymer grade having a low residual concentration of water.

The condensed stream of technical acrylic acid 5 is introduced into a first intermediate distillation column 29, at a point located between the column top and bottom, preferably at the level of a plate located in the upper half of the column 29.

The introduction of the chemical agent 22 is carried out into the stream of technical acrylic acid 5 feeding this intermediate column 29 or at a point located between the feeding of the said column and the column bottom. The water generated by the reaction for the treatment of the aldehydes is entrained with the gaseous top stream 30 from the column 29, which is subsequently condensed in an exchanger 31 before being, in part, drawn off (stream 32) and, in part, sent back as reflux into the column.

The stream 32 is composed essentially of acrylic acid and contains a low concentration of water. It can be sent back upstream into the process or can be used, for example for the manufacture of esters.

The stream 33 obtained at the column 29 bottom is, in part, sent back into the column through the boiler 34, the other portion feeding a second purification column 21. A liquid stream 25 of polymer-grade acrylic acid freed from water is obtained at the top of this purification column 21; after condensation in the exchanger 24, a portion of this liquid stream is sent back as reflux into the column 21. The heavy products formed and heavy inhibitors are removed in the bottom stream 28 from the column 21.

The two purification columns 29 and 21 are preferably operated under reduced pressure.

The purification columns 21 and 29 can be of various configurations.

The column 21 of the two embodiments illustrated in FIGS. 3 and 4 is a conventional distillation column generally comprising from 5 to 30 theoretical plates, preferably from 8 to 20 theoretical plates. This distillation column is combined with a reboiler and a condenser.

The purification column 29 of the embodiment illustrated in FIG. 4 is a conventional distillation column generally comprising from 1 to 20 theoretical plates, preferably from 5 to 15 theoretical plates. This distillation column is combined with a reboiler and a condenser.

Just like the embodiments in which the chemical treatment agent 22 is introduced into the purification section comprising the dehydration column and the finishing column, the mixing of the stream to be treated and of the chemical agent can optionally be carried out in an intermediate tank or a group of intermediate tanks in series, prior to its introduction into the column 21 (FIG. 3) or 29 (FIG. 4).

Likewise, following the example of the specific embodiment of a purification carried out in a group comprising only two successive dehydration and finishing columns, it is possible to carry out a second drawing off of a sidestream in the gas phase on the finishing column 17, at a position located below the drawing off of a sidestream of purified (technical-grade) acrylic acid. This stream corresponds to an acrylic acid of ester grade devoid of heavy byproducts, which are concentrated in the bottom stream 9 of the finishing column. It can advantageously be made use of economically as starting material of an esterification process for producing different acrylic esters.

It is apparent, surprisingly, that the problems of formation of solids do not appear in the process according to the invention, while the ratios of concentration by weight of furfural to acrolein present in the acrylic acid streams into which the chemical treatment agent is introduced are different from those shown in patent EP 1110940, making it possible to avoid the generation of solid polymers. Without being committed to this explanation, the inventors believe that the agent for the chemical treatment of the aldehydes is introduced optimally into a stream of crude acrylic acid having a composition better suited to the dissolution of the reaction byproducts (preferred embodiment carried out in a plant comprising only two distillation columns) or into a stream of technical acrylic acid of better quality than the technical grades available according to the conventional processes of the prior art (embodiment with chemical treatment of the technical acrylic acid in an additional section).

The process according to the invention in all its alternative forms makes it possible to produce glacial or polymer-grade acrylic acid having a content by weight of acrylic acid >99%, preferably >99.5%, and preferably comprising a content of total aldehydes <10 ppm, indeed even <3 ppm. The polymer-grade acrylic acid obtained according to the process of the invention likewise preferably has the contents of following impurities:
protoanemonin <5 ppm, in particular <3 ppm
maleic anhydride <100 ppm, in particular <50 ppm
non-phenolic polymerization inhibitors <10 ppm, in particular <3 ppm.

The plant according to the invention, adapted for carrying out the process for the recovery of polymer-grade (meth) acrylic acid as described, comprises at least:
a) one dehydration column;
b) one finishing column fluidically connected at the bottom of the said dehydration column;
c) optionally at least one distillation column fluidically connected laterally to the said finishing column;
d) a mixing device ensuring the introduction, the mixing and the optimum conditions for reaction of a chemical treatment agent in the dehydration column bottom stream feeding the finishing column, optionally comprising an intermediate tank;
e) at least one system for drawing off a sidestream for the finishing column.

Mention may be made, as mixing devices which can be used, of a stirred or recirculated vessel, or an in-line mixer, optionally in combination with an intermediate storage tank. The mixing device makes it possible to ensure a minimum residence time, generally of between 5 min and 120 min, and to set an optimum temperature generally of between 30° C. and 80° C., in order for the reaction of the chemical treatment agent with the impurities, in particular of aldehyde type, to be most effective, without bringing about the deposition of solid.

Another subject-matter of the invention relates to a process for the production of polymer-grade (meth)acrylic acid comprising at least the following stages:
A) at least one (meth)acrylic acid precursor is subjected to gas-phase oxidation in order to form a gaseous reaction mixture comprising (meth)acrylic acid;
B) the gaseous reaction mixture is cooled;
C) the cooled gaseous reaction mixture is subjected to the process for the recovery of (meth)acrylic acid as defined above.

The precursor of the (meth)acrylic acid can be acrolein or methacrolein and can be derived from a renewable starting material, thus producing biobased (meth)acrylic acid.

Preferably, the (meth)acrylic acid is acrylic acid and the precursor of the acrylic acid is acrolein obtained by catalytic oxidation of propylene.

The oxidation reaction of stage A), carried out according to the knowledge of the art, generally provides a gaseous reaction mixture, overheated at a temperature of greater than 280° C.

This mixture is advantageously cooled according to a stage B), in particular down to a temperature less than 250° C., preferably less than 190° C., in order to be subjected, according to stage C), to the process for the recovery of the (meth)acrylic acid without using an azeotropic solvent and including a chemical treatment for the removal of the aldehydes. It can be cooled directly in the dehydration column or can be cooled using a heat exchanger located upstream of the dehydration column.

The process according to the invention provides a polymer-grade (meth)acrylic (or GAA) which can be used to prepare acrylic superabsorbents intended for the fields of hygiene or cable manufacture, or high-purity acrylic esters, or also acrylic dispersants or flocculants comprising a low content of volatile organic compounds.

The invention will now be illustrated by the following examples, which do not have the aim of limiting the scope of the invention defined by the appended claims.

EXPERIMENTAL PART

The percentages are expressed as percentages by weight.
In the examples which follow, the following analytical methods were used:
High performance liquid chromatography on an Atlantis DC 18 column supplied by Waters, with UV detection and external calibration: furfural, benzaldehyde, maleic anhydride assayed in the form of maleic acid, acetic acid and phenothiazine,
UV-visible spectrometry, after reaction of acrolein with 4-hexylresorcinol in an ethanol/triachloroacetic acid medium, catalyzed by mercuric chloride, and development of a blue coloration exhibiting a maximum absorbance at 603 nm: acrolein.

Example 1 (Comparative)

Simulations using ASPEN software have been used to illustrate a process according to the prior art. It is in particular the process described in patent EP 2 066 613 B1, which provides, by drawing off a sidestream from the column 17, a stream 5 of purified acrylic acid as represented in FIG. 3.

The flow rates, temperatures, pressures and compositions in main compounds of the streams are given in the table below:

| | Stream No. | | | | | | |
|---|---|---|---|---|---|---|---|
| | 1 | 14/15 | 3 | 11 | 8 | 5 | 6 |
| Flow rate (kg/h) | 70501 | 59058 | 49800 | 335709 | 37642 | 11000 | 1195 |
| Pressure (bar abs) | 1.36 | 1.12 | 0.12 | 1.40 | 0.12 | 0.21 | 0.24 |

-continued

| | Stream No. | | | | | | |
|---|---|---|---|---|---|---|---|
| | 1 | 14/15 | 3 | 11 | 8 | 5 | 6 |
| Temperature (° C.) | 181 | 59 | 62 | 100 | 73 | 96 | 102 |
| Composition | | | | % by weight | | | |
| Noncondensable compounds | 73.36% | 87.56% | 0.016% | 0.014% | 0.102% | 0.058% | <0.001% |
| $H_2O$ | 8.51% | 10.83% | 4.40% | 4.56% | 5.86% | 0.00% | 0.00% |
| Acrylic acid | 16.70% | 0.26% | 85.01% | 84.54% | 80.62% | 99.81% | 84.18% |
| Acetic acid | 0.56% | 0.65% | 10.05% | 10.41% | 13.29% | 0.05% | <0.001% |
| Furfural | 0.0051% | <0.001% | 0.0112% | 0.0105% | 0.0052% | 0.0142% | 0.1690% |
| Benzaldehyde | 0.0085% | <0.001% | 0.0154% | 0.0142% | 0.0049% | 0.0082% | 0.4141% |
| Acrolein | 0.1976% | 0.2341% | 0.0280% | 0.0287% | 0.0371% | <0.001% | <0.001% |
| Maleic acid + anhydride | 0.15% | <0.001% | 0.23% | 0.21% | 0.03% | 0.04% | 7.11% |
| Acrylic acid dimer | 0.12% | 0.00% | 0.16% | 0.14% | <0.001% | <0.001% | 6.79% |

In this table, it is apparent that the ratio of concentration by weight of furfural to acrolein is well below three in the stream 3 and the quality of purified acrylic acid obtained by drawing off a sidestream from the column 17 (stream 5) is not of sufficient quality to be used in an application requiring a quality of acrylic acid of polymer grade. In particular, the concentrations of furfural and benzaldehyde and maleic acid/anhydride are too great to manufacture polymers having a high molecular weight corresponding to the wishes of the applicators.

Example 2 (Reference)

A synthetic mixture representative of the medium obtained at the bottom of the dehydration column of a process for the purification of acrylic acid not using an external organic solvent is prepared. This synthetic stream has the following composition: acrylic acid (85.20%), acetic acid (10%), water (4.4%), acrolein (0.03%), furfural (0.011%), benzaldehyde (0.015%), maleic anhydride (0.2%), phenothiazine (0.1%) and hydroquinone (0.05%).

250 g of this mixture are introduced into a round-bottomed glass flask and the mixture is distilled in a rotary evaporator at a temperature of 90° C. under a pressure of 30 mbar, so as to collect approximately 80% of distilled fraction.

After evaporation, 201 g of colourless and clear distillate are collected, which distillate assays 0.01% furfural, 0.01% benzaldehyde, 0.03% acrolein and 0.15% maleic acid/anhydride.

The results of this test reflect the distribution of the impurities under flash distillation conditions, without a separating plate. It acts as reference for the following tests carried out in the presence of chemical agents for the treatment of aldehydes.

Example 3 (According to the Invention)

The same treatment as Test 2 is repeated starting from 200 g of the same synthetic mixture but this time adding 0.35 g of hydrazine hydrate. In addition, the mixture is first brought to 40° C. for 60 minutes at atmospheric pressure and then distilled in the rotary evaporator at a temperature of 90° C. under a pressure of 30 mbar.

154 g (77%) of colourless and clear distillate are recovered, which distillate assays <1 ppm furfural, <1 ppm benzaldehyde, <1 ppm acrolein and <1 ppm of maleic acid/anhydride.

The nondistilled residue collected after evaporation is clear and without a solid deposit.

Example 4 (According to the Invention)

The same treatment as Test 3 is repeated, starting from 200 g of synthetic mixture described in Test 2 but this time adding 0.31 g of aminoguanidine bicarbonate.

After evaporation, 152 g (76%) of colourless and clear distillate are collected, which distillate assays <1 ppm furfural, <1 ppm benzaldehyde, <1 ppm acrolein and 48 ppm of maleic acid/anhydride.

The nondistilled residue collected after evaporation is clear and without a solid deposit.

Example 5 (According to the Invention)

The same treatment as Test 3 is repeated, starting from 200 g of synthetic mixture described in Test 2 but this time adding 0.47 g of meta-phenylenediamine.

After evaporation, 157 g (78%) of colourless and clear distillate are collected, which distillate assays <1 ppm furfural, 3 ppm benzaldehyde, <1 ppm acrolein and 7 ppm of maleic acid/anhydride.

The nondistilled residue collected after evaporation is clear and without a solid deposit.

Examples 3, 4 and 5 show that it is possible to obtain, starting from a stream representative of a dehydration column bottom product obtained according to a recovery/purification process without the addition of a solvent, a quality of acrylic acid of polymer grade, without an additional distillation stage, by virtue of a treatment with a chemical agent.

Example 6 (Reference)

A synthetic mixture representative of the medium obtained at the bottom of the dehydration column of a process for the purification of acrylic acid not using an organic solvent is prepared. This synthetic stream has the following composition: acrylic acid (84.6%), acetic acid (9.7%), formic acid (0.1%), water (4.3%), acrolein (0.027%), furfural (0.010%), benzaldehyde (0.015%), maleic anhydride (0.20%) and phenothiazine (0.1%).

This synthetic mixture is introduced continuously at a flow rate of 289 g/h into a 500 ml glass reactor maintained at a constant level, heated at 50° C., under constant and vigorous stirring. The temperature regulated in the reactor is at 50° C. and the residence time of the mixture in this stirred tank is 1 hour.

The reaction mixture exiting from the reactor feeds a thermosiphon reboiler heated by electrical resistance.

Under the flash distillation conditions operated in the reboiler, under a pressure of 345 hPa, at a temperature of 101° C., a top stream representing 90% of the feed stream is distilled.

The analysis of the top stream indicates a concentration of furfural of 113 ppm and the bottom stream comprises 163 ppm of furfural. No manifest fouling is observed.

This example shows that, in the absence of chemical additive reacting with the aldehydes, the furfural is divided between the top stream and the bottom stream, and the quality of the top stream is not satisfactory.

Example 7 (According to the Invention)

The experiment described in Example 6 is performed again under the same conditions but in the presence of a treatment agent for the removal of the aldehydes.

The synthetic mixture with a composition identical to that of Example 6 is introduced continuously at a flow rate of 235 g/h into the reactor heated at 50° C. 0.78 g/h of hydrazine hydrate are also introduced into this reactor. The residence time of the mixture in the reactor is equal to one hour. The amount of chemical agent added corresponds to a molar ratio of 2 with respect to the sum of the aldehydes present in the medium to be treated.

The reaction mixture exiting from the reactor feeds the thermosiphon reboiler under a pressure of 276 hPa. Subsequent to the flash distillation, there are obtained, after condensation, 219 g/h of liquid distillate (93% of the stream feeding the boiler) and 16 g/h of bottom stream.

After analysis of the top stream, the concentration of furfural (the most difficult impurity to separate because it is the closest to acrylic acid in terms of boiling point) is 1 ppm.

In this mixture, the ratio of the concentration of furfural/acrolein in the feed stream is 0.4. Although this ratio clearly lies outside the interval of 3 to 100 specified in Patent EP 1 110 940 as being optimum, this example shows that the removal of the furfural is effective. Furthermore, no manifest fouling is observed in the setup.

Example 8 (According to the Invention)

The experiment described in Example 7 is performed again under the same conditions but the chemical treatment agent introduced into the reactor is a 20% solution of aminoguanidine bicarbonate prepared in glacial acrylic acid (devoid of aldehyde impurities).

The synthetic mixture with a composition identical to that of Example 7 (235 g/h) and the solution of chemical agent for the treatment of the aldehydes (11.8 g/h) are introduced with vigorous stirring into the reactor maintained at 50° C., with a residence time of one hour. The amount of chemical agent added corresponds to a molar ratio of 2.2 with respect to the sum of the aldehydes present in the medium to be treated. The reaction mixture extracted from the reactor is sent as feed to the reboiler, operated at a temperature of 101° C. under 315 hPa. A top stream corresponding to 84% of the feed stream is distilled.

After analysis, the top stream comprises 1 ppm of furfural. No significant fouling of the item of equipment is observed.

The invention claimed is:

1. A process for the recovery of polymer-grade (meth) acrylic acid, in the absence of organic solvent, from a gaseous reaction mixture comprising (meth)acrylic acid obtained by gas-phase oxidation of a precursor of the (meth)acrylic acid, comprising at least the following stages:

i) subjecting the gaseous reaction mixture to dehydration without using azeotropic or external organic solvent in a first distillation column, referred to as dehydration column having an upper part and a lower part, a temperature of the upper part being at least 40° C., said dehydration column operating at atmospheric pressure or greater pressure, resulting in a top stream, at least a portion of which is condensed and sent back to the dehydration column in the form of reflux, and in a bottom stream;

ii) subjecting the dehydration column bottom stream at least in part, to distillation in a second column, referred to as finishing column, resulting in a top stream comprising water and in a bottom stream comprising heavy compounds;

iii) recovering a purified polymer-grade (meth)acrylic acid stream by drawing off a sidestream from the finishing column;

wherein said process is carried out in the presence of at least one agent for the chemical treatment of aldehydes for reducing content of residual heavy aldehydes having a boiling point greater than that of (meth)acrylic acid and light aldehydes having a boiling point lower than that of (meth)acrylic acid;

wherein the finishing column is a column having a separating wall having two sides which is fed, on one side of the wall, with the dehydration column bottom stream and the drawing off of a sidestream of the purified (meth)acrylic acid stream is carried out in a section located on the other side of the separating wall;

wherein the agent for the chemical treatment of the heavy and light aldehydes is introduced into the finishing column at a level of a section located between the feed level of said finishing column and the level of a plate for drawing off a sidestream of purified (meth)acrylic acid; and wherein a second drawing off is carried out in the gas phase on the finishing column, at a position located below the drawing off of a sidestream of the purified acrylic acid.

2. The process according to claim 1, wherein the finishing column is a distillation column operating at a pressure below atmospheric pressure.

3. The process according to claim 1 wherein the purified (meth)acrylic acid stream obtained in stage iii) is drawn off in the form of a gaseous stream of polymer-grade (meth) acrylic acid.

4. The process according to claim 1 wherein the purified (meth)acrylic acid stream drawn off in stage iii) is subjected to an additional treatment by distillation using one or two distillation columns and the agent for the chemical treatment of the aldehydes is introduced during said additional treatment.

5. The process according to claim 1 wherein the agent for the chemical treatment of the aldehydes is chosen from the group consisting of:
    amines,
    aniline and aniline compounds,
    hydrazine, hydrazine compounds, hydrazine salts, aminoguanidine and its salts
    hydrazides, hydrazides of carboxylic acids and their salts, dihydrazides of adipic acid and succinic acid, urea and derivatives of urea and of hydrazine, and their salts;
    alone or their mixtures in all proportions.

6. The process according to claim 1 wherein the precursor of the (meth)acrylic acid is acrolein, obtained by oxidation of propylene or by oxydehydrogenation of propane.

7. The process according to claim 1 wherein the precursor of the (meth)acrylic acid is methacrolein, obtained by oxidation of isobutylene and/or of tert-butanol or from oxydehydrogenation of butane and/or isobutane.

8. The process according to claim 1 wherein the precursor of the (meth)acrylic acid comprises carbon of renewable origin and is derived from glycerol, 3-hydroxypropionic acid or 2-hydroxypropionic acid.

* * * * *